US012649908B2

(12) United States Patent
Fu et al.

(10) Patent No.: US 12,649,908 B2
(45) Date of Patent: Jun. 9, 2026

(54) CELL LINES FOR PRODUCTION OF ADENO-ASSOCIATED VIRUS

(71) Applicant: The University of North Carolina at Chapel Hill, Chapel Hill, NC (US)

(72) Inventors: Haiyan Fu, Durham, NC (US); Xinghua Zeng, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 484 days.

(21) Appl. No.: 18/256,530

(22) PCT Filed: Dec. 8, 2021

(86) PCT No.: PCT/US2021/062296
§ 371 (c)(1),
(2) Date: Jun. 8, 2023

(87) PCT Pub. No.: WO2022/125601
PCT Pub. Date: Jun. 16, 2022

(65) Prior Publication Data
US 2024/0026309 A1      Jan. 25, 2024

Related U.S. Application Data

(60) Provisional application No. 63/123,462, filed on Dec. 9, 2020.

(51) Int. Cl.
*C12N 7/02*      (2006.01)
*C12N 5/071*      (2010.01)

(52) U.S. Cl.
CPC ........... *C12N 7/025* (2013.01); *C12N 5/0686* (2013.01); *C12N 2750/14143* (2013.01); *C12N 2750/14151* (2013.01)

(58) Field of Classification Search
CPC ...................................................... C12N 7/025
See application file for complete search history.

(56) References Cited

U.S. PATENT DOCUMENTS

| | | | |
|---|---|---|---|
| 9,441,206 B2 * | 9/2016 | Grieger | C12N 7/00 |
| 2016/0024480 A1 | 1/2016 | Hwang et al. | |
| 2016/0222356 A1 | 8/2016 | Zhao et al. | |

FOREIGN PATENT DOCUMENTS

| | | |
|---|---|---|
| EP | 2771455 B1 | 10/2016 |
| WO | 2012109214 A1 | 8/2012 |

OTHER PUBLICATIONS

"International Search Report and Written Opinion corresponding to International Application No. PCT/US2021/062296 mailed Mar. 29, 2022".
Wright, J. Fraser, "Transient Transfection Methods for Clinical Adeno-Associated Viral Vector Production", Human Gene Therapy 20:698-706 (Jul. 2009).
"International Preliminary Report on Patentability corresponding to International Application No. PCT/US2021/062296 mailed Jun. 22, 2023".

* cited by examiner

*Primary Examiner* — Mark L Shibuya
(74) *Attorney, Agent, or Firm* — Myers Bigel, P.A.

(57) ABSTRACT

This invention relates to a HEK-293 cell line that grows under animal component-free suspension conditions. This invention further relates a HEK-293 cell line that grows under adherent conditions. The cell lines may provide rapid and scalable production of adenoassociated virus (AAV) and support production of all serotypes and chimera of AAV.

21 Claims, No Drawings

CELL LINES FOR PRODUCTION OF ADENO-ASSOCIATED VIRUS

STATEMENT OF PRIORITY

This application is a 35 U.S.C. § 371 national phase application of PCT Application PCT/US2021/062296 filed Dec. 8, 2021, which claims the benefit, under 35 U.S.C. § 119(e), of U.S. Provisional Application Ser. No. 63/123,462, filed on Dec. 9, 2020, the entire contents of each of which are incorporated by reference herein in their entireties.

FIELD OF THE INVENTION

The present invention relates to HEK-293 cell lines that grow in suspension conditions and HEK-293 cell lines that grow in adherent conditions. The present invention also relates to HEK-293 cell lines that may be useful for the scalable production of adeno-associated virus (AAV) for gene therapy.

BACKGROUND OF THE INVENTION

Recombinant adeno-associated virus (rAAV) vectors have demonstrated transduction and long-term gene expression with little to no toxicity and inflammation in vivo. These unique characteristics of AAV have led to its recognition as a leading vector candidate for gene therapy applications. A number of Phase I and Phase II clinical trials utilizing AAV have been performed worldwide (See, e.g., Aucoin et al., *Biotechnol. Adv.* 26:73 (2008) and Mueller et al., *Gene Ther.* 15:858 (2008)). However, many preclinical studies and successful clinical trials have identified challenges that will need to be addressed to sustain rAAV use for human gene therapy (See, Mueller et al., *Gene Ther.* 15:858 (2008)). One significant challenge is establishing large scale manufacturing technologies in accordance with current Good Manufacturing Practices (cGMP) to yield the purified vector in quantities needed for the expanding clinical demand. The success of scalable production technology relies heavily on understanding the basic biology of AAV to produce reagents such as cell lines, plasmids or recombinant viral vectors, etc. that when used together, will closely mimic wild-type AAV production.

AAV has been classified as a dependovirus in the Parvovirus family because it requires coinfection with helper viruses such as adenovirus (Ad) or herpes simplex virus (HSV) for productive infection in cell culture (See, Atchison et al., *Science* 149:754 (1965); Buller et al., *J. Virol.* 40:241 (1981)). Parvoviruses are among the smallest of the DNA animal viruses with a virion of approximately 25 nm in diameter composed entirely of protein and DNA. The AAV genome is a linear, single-stranded DNA molecule containing 4679 bases (See, Srivastava et al., *J Virol.* 45:555 (1983)). The wild-type (wt) AAV genome is made up of two genes that encode four replication proteins and three capsid proteins, respectively, and are flanked on either end by inverted terminal repeats (ITRs) (See, Lusby et al., *J. Virol.* 4:402 (1980) and Srivastava et al., *J. Virol.* 45:555 (1983)). The ITRs are the only cis-acting elements necessary for genome replication and packaging into the capsid. The four replication proteins (Rep 78, 68, 52 and 40) are multifunctional and play a role in transcription, viral DNA replication and DNA packaging into the preformed viral capsid within the nucleus of the infected cell (See, Chejanovsky et al., *Virology* 173:120 (1989) and King et al., *EMBO J.* 20:3282 (2001)). The viral capsid is made up of the three proteins Vp1, Vp2 and Vp3 in a ratio of 1:1:8 respectively. The capsid proteins are produced from the same open reading frame (ORF) but utilize different translational start sites.

Because the ITRs are the only cis acting elements necessary for genome replication and packaging, the replication (rep) and capsid (cap) genes can be removed and cloned into a separate plasmid without a loss in function. A promoter and gene of interest driven by a promoter can then be cloned between the ITRs. Thus, any gene that is flanked by the ITRs can effectively be packaged into an AAV capsid as long as the genome is smaller than 5.0 kb in size (See, Dong et al., *Mol. Ther.* 18:87 (2010), Grieger et al., *J. Virol.* 79:9933 (2005), and Wu et al., *Mol. Ther.* 18:80 (2010)). However, AAV still lacks the ability to replicate. One of the distinctive features of AAV is the requirement of co-infection with a helper virus such as Ad or HSV.

The generation of rAAV previously required transfection of the vector and packaging constructs into Ad-infected cells (See, Muzyczka, Curr. *Top. Microbiol. Immunol.* 158:97 (1992)). Upon co-infection with Ad or HSV, AAV utilizes several helper virus early genes to facilitate its own replication. Infection of Ad into producer cells to generate rAAV was effective in producing rAAV, but it also produced an overabundance of Ad particles. Removal of Ad has required physical techniques such as CsCl gradients, column chromatography, and a heat-denaturing step to inactivate any residual Ad particles that may still be present. While most of these procedures have succeeded to various degrees, the potential for Ad contamination is an unwanted risk and the presence of Ad denatured proteins may be unacceptable for clinical use.

A significant improvement in the evolution of rAAV production was the introduction of the triple plasmid transfection (Xiao et al., *J. Virol.* 72:2224 (1998)). This method used a variation of the rep and cap plasmid as well as the ITR plasmid but eliminated the use of Ad infection. The Ad proteins of E1A, E1B, E4 and E2A and VA RNA were cloned into a single plasmid called XX680. Supplying the Ad helper genes on the XX680 plasmid eliminated Ad production in the transfected cells yielding only rAAV vector.

Advances in rAAV production have allowed a number of laboratories to move away from production using adherent HEK-293 cells and move toward scalable technologies such as infection-based technologies through the use of recombinant adenovirus (See, Gao et al., *Mol. Ther.* 5:644 (2002); Gao et al., *Hum. Gene Ther.* 9:2353 (1998); Liu et al., *Mol. Ther.* 2:394 (2000); Liu et al., *Gene Ther.* 6:293 (1999); and Tessier et al., *J. Virol.* 75:375 (2001)), herpes simplex virus (See, Booth et al., *Gene Ther.* 11:829 (2004); Conway et al., *Gene Ther.* 6:986 (1999); Hwang et al., *Mol. Ther.* 7:S14 (2003); Kang et al., *Gene Ther.* 16:229 (2009); and Thomas et al., *Hum. Gene Ther.* 20:861 (2009)), baculovirus expression vector system (BEVS) (See, Aslanidi et al., *Proc. Natl. Acad. Sci. USA* 106:5059 (2009); Cecchini et al., *Gene Ther.* 15:823 (2008); Kohlbrenner et al., *Mol. Ther.* 12:1217 (2005); Negrete et al., *Meth. Mol. Biol.* 433:79 (2008); Negrete et al., *J Gene Med.* 9:938 (2007); Urabe et al., *Hum. Gene Ther.* 13:1935 (2002); and Urabe et al., *J Virol.* 80:1874 (2006)), and transient transfection of suspension HEK-293 cells (Durocher et al., *J Virol. Meth.* 144:32 (2007); Hildinger et al., *Biotechnol. Lett.* 29:1713 (2007); and Park et al., *Biotechnol. Bioeng.* 94:416 (2006)). Park et al. and Durocher et al. demonstrated that approximately $1.4 \times 10^4$ and $3 \times 10^4$ vg/cell, respectively, were generated using their optimized serum-free suspension HEK-293 cell production systems. Common with these studies is the fact that the yield of vector continues to be the impediment and is significantly below the vg/cell generated via transfection of adherent HEK-293 cells and the rHSV production system.

SUMMARY OF THE INVENTION

Provided according to some embodiments of the invention is an isolated HEK-293 cell that is deposited as ATTC No. PTA-127160. Such cells may grow in suspension condition free of animal components. Also provided is a master cell bank including the HEK-293 cells deposited as ATTC No. PTA-127160.

Also provided according to some embodiments of the invention is an isolated HEK-293 cell that is deposited as ATTC No. PTA-127161. Such cells may grow in adherent culture conditions. Also provided is a master cell bank including the HEK-293 cells deposited as ATTC No. PTA-127161.

Further provided according to embodiments of the invention are methods of producing AAV particles. In some embodiments, such methods include providing to HEK-293 cells deposited as ATTC No. PTA-127160 or ATCC No. PTA-127161 to an AAV expression system, culturing the cells under conditions in which AAV particles are produced, and optionally, isolating the AAV particles.

These and other aspects of the invention are set forth in more detail in the description of the invention below.

DETAILED DESCRIPTION OF THE INVENTION

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual*, 99-102 (November 1990) (U.S. Patent and Trademark Office).

Except as otherwise indicated, standard methods known to those skilled in the art may be used for the construction of rAAV constructs, packaging vectors expressing the AAV Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N Y, 1989); AUSUBEL et al.

CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

Definitions

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 10%, 5%, 1%, 0.5%, or even 0.10% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps and those that do not materially affect the basic and novel characteristic(s) of the claimed invention (e.g., rAAV replication). Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al. VIROLOGY, volume 2, chapter 69 (4th ed., Lippincott-Raven Publishers).

The genus Dependovirus contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al. VIROLOGY, volume 2, chapter 69 (4th ed., Lippincott-Raven Publishers); and Table 1.

TABLE 1

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |

TABLE 1-continued

| AAV Serotypes/Isolates | GenBank Accession Number |
| --- | --- |
| Bovine AAV | NC_005889, AY388617 |
| AAV4 | NC_001829 |
| AAV5 | AY18065, AF085716 |
| Rh34 | AY243001 |
| Rh33 | AY243002 |
| Rh32 | AY243003 |
| AAV10 | AY631965 |
| AAV11 | AY631966 |
| AAV12 | DQ813647 |
| AAV13 | EU285562 |
| Clade A | |
| AAV1 | NC_002077, AF063497 |
| AAV6 | NC_001862 |
| Hu. 48 | AY530611 |
| Hu 43 | AY530606 |
| Hu 44 | AY530607 |
| Hu 46 | AY530609 |
| Clade B | |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC_001863 |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |

TABLE 1-continued

| AAV Serotypes/Isolates | GenBank Accession Number |
| --- | --- |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

As used herein, the term "adeno-associated virus (AAV)," includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROL-OGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The genomic sequences of various serotypes of AAV, as well as the sequences of the native ITRs, Rep proteins, and capsid subunits are known in the art. Such sequences may be found in the literature or in public databases such as Gen- Bank. See, e.g., GenBank Accession Numbers NC 002077, NC_001401, NC_001729, NC 001863, NC 001829, NC_001862, NC 000883, NC_001701, NC_001510, NC 006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching AAV nucleic acid and amino acid sequences. See also, e.g., Bantel-Schaal et al., *J. Virol.* 73:939 (1999); Chiorini et al., *J. Virol.* 71:6823 (1997); Chiorini et al., *J. Virol.* 73:1309 (1999); Gao et al., *Proc. Nat. Acad. Sci. USA* 99:11854 (2002); Moris et al., *Virology,* 33:375 (2004); Mori et al., *Virology,* 330:375 (2004); Muramatsu et al., *Virology,* 221: 208 (1996); Ruffing et al., *J. Gen. Virol.* 75:3385 (1994); Rutledge et al., *J. Virol.* 72:309 (1998); Schmidt et al., *J. Virol.* 82:8911 (2008); Shade et al., *J. Virol.* 58:921 (1986); Srivastava et al., *J. Virol.* 45:555 (1983); Xiao et al., *J. Virol.* 73:3994 (1999); international patent publications WO 00/28061, WO 99/61601, WO 98/11244; and U.S. Pat. No. 6,156,303; the disclosures of which are incorporated by reference herein for teaching AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, PA (incorporated herein it its entirety).

The term "tropism," as used herein, refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by an AAV means that the AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (4th ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide) and can be either single or double stranded DNA sequences.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components (e.g., cell wall or cell membrane) or other polypeptides or nucleic acids commonly found associated with the polynucleotide. In some embodiments, an isolated polynucleotide is one that is at least about 20% pure, e.g., at least about 30, 40, 50, 60, 70, 80, 90, or 95% pure.

Likewise, an "isolated" polypeptide means a polypeptide that is separated or substantially free from at least some of the other components of the naturally occurring organism or virus, for example, the cell or viral structural components (e.g., cell wall or cell membrane) or other polypeptides or nucleic acids commonly found associated with the polypeptide. In some embodiments, an isolated polypeptide is one that is at least about 20% pure, e.g., at least about 30, 40, 50, 60, 70, 80, 90, or 95% pure.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

The terms "heterologous nucleotide sequence" and "heterologous nucleic acid" are used interchangeably herein and refer to a sequence that is not naturally occurring in the virus.

Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed AAV particles as described in international patent publication WO 01/92551 (the disclosure of which is incorporated herein by reference in its entirety). Thus, in some embodiments, double stranded (duplex) genomes can be packaged into the virus capsids.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (See, Muzyczka, *Curr. Topics Microbiol. Immunol.* 158:97 (1992)).

Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In some embodiments of the invention, the rAAV genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

An "AAV expression system" is a system of one or more polynucleotides that are sufficient, when introduced into a suitable host cell, to support production of rAAV. An AAV expression system will typically include polynucleotides encoding AAV rep and cap, helper genes, and a rAAV genome. One example of an AAV expression system is the triple plasmid transfection method.

The term "terminal repeat" or "TR" includes any viral terminal repeat or synthetic sequence that forms a hairpin structure and functions as a terminal repeat (i.e., mediates the desired functions such as replication, virus packaging, integration and/or provirus rescue, and the like). The TR can be an inverted terminal repeat (ITR) such as an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al.

AAV genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

Virus vectors can further be "targeted" virus vectors (e.g., having a directed tropism) and/or a "hybrid" AAV (i.e., in which the viral ITRs and viral capsid are from different AAV or other parvoviruses) as described in international patent publication WO 00/28004 and Chao et al., *Mol. Therapy* 2:619 (2000). In other embodiments, the virus vectors are "chimeric" AAV (i.e., in which the capsid proteins are from more than one serotype and/or the capsid proteins are modified to contain sequences from more than one serotype).

Further, the viral capsid or genomic elements can contain other modifications, including insertions, deletions and/or substitutions.

The term "template" or "substrate" is used herein to refer to a polynucleotide sequence that may be replicated to produce the AAV viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like).

Alternatively, the template may be stably incorporated into the chromosome of a packaging cell.

As used herein, AAV "Rep coding sequences" indicate the nucleic acid sequences that encode the AAV non-structural proteins that mediate viral replication and the production of new virus particles. The AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the AAV Rep proteins. For example, with respect to AAV, the Rep coding sequences do not need to encode all four AAV Rep proteins (Rep78, Rep68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (See, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, the AAV p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (See, e.g., Urabe et al., *Hum. Gene Ther.* 13:1935 (2002)).

As used herein, the AAV "cap coding sequences" encode the structural proteins that form a functional AAV capsid (i.e., can package DNA and infect target cells). Typically, the cap coding sequences will encode all of the AAV capsid subunits, but less than all of the capsid subunits may be encoded as long as a functional capsid is produced. Typically, but not necessarily, the cap coding sequences will be present on a single nucleic acid molecule. The capsid structure of AAV is described in more detail in BERNARD N. FIELDS et al., VIROLOGY, volume 2, chapters 69 & 70 (4th ed., Lippincott-Raven Publishers).

As used herein, the term "animal component-free" refers to a culture medium or other composition that does not contain any product extracted or purified from animals or animal cells, including serum, enzymes, carbohydrates, nucleic acids, proteins, antibodies, extracellular matrix, etc.

Suspension HEK-293 Cell Line

In an effort to generate a scalable manufacturing technology to produce a relatively high titer and relatively pure rAAV, a HEK-293 cell line that grows under animal component-free suspension conditions was developed. The cell line was developed from an adherent HEK-293 cell line from the American Type Culture Collection (ATCC). After adaption to growth in animal-component free suspension conditions, the resulting suspension HEK-293 cell line maintained its ability for efficient transfection and rAAV production.

Thus, in some embodiments of the invention, provided is an isolated HEK-293 cell deposited under the Budapest Treaty on Nov. 5, 2021 (ATCC Deposit No. PTA-127160). Further provided in embodiments of the invention are suspension cell cultures that include HEK-293 cells deposited under ATCC Deposit No. PTA-127160. As used herein, HEK-293 cells deposited under ATCC Deposit No. PTA-127160 may also be referred to as the "suspension HEK-293 cells of the invention." Also provided is a master cell bank including cells deposited as ATCC No. PTA-127160. In some embodiments of the invention, the HEK-293 master cell bank may be GMP-compliant (See, 21 CFR 210/211, 2003/94/EC).

In some embodiments of the invention, a cell line including the suspension HEK-293 cells of the invention may be suitable for culturing in any volume of culture medium, from 10 ml (e.g., in shaker flasks) to 10 L, 50 L, 100 L, or more (e.g., in bioreactors). The cell line is suitable for production of all serotypes, chimeras, and hybrids of AAV, e.g., AAV1, AAV2, AAV3, AAV4, AAV5, AAV6, AAV7, AAV8, AAV9, AAV10, AAV11, AAV12, AAV13, any AAV now known or later discovered, and any chimeras and/or hybrids thereof, e.g., AAV1-13 2.5, 2i8, 9.45 and other chimeric or hybrid capsids.

Any suitable suspension culturing method now known or later discovered may be used to culture the suspension HEK-293 cells of the invention. In some embodiments, the suspension HEK-293 cells of the invention are cultured in animal component-free conditions. The animal component-free medium can be any animal component-free medium (e.g., serum-free medium) compatible with HEK-293 cells. Examples include, without limitation, SFM4Transfx-293 (Hyclone), Ex-Cell 293 (JRH Biosciences), LC-SFM (Invitrogen), and Pro293-S (Lonza), and Freestyle™ F-17 (Gibco).

In some embodiments of the invention, cells are cultured by suspending cells in a suspension growth media (e.g., Freestyle™ F-17 (Gibco)) and incubating the cells, for example, in a shaker and/or bioreactor. In some embodiments, cells are incubated at a temperature in a range of about 35 to about 40° C. (e.g., 37° C.) in a shaker for 24, 32, 40, 48 hours or more and/or incubated in suspension growth media in a bioreactor for 24, 32, 40, 48 hours or more. A non-limiting example of a shaker is the Multitron Incubator Shaker and a non-limiting example of a bioreactor is the Wave Bioreactor™ 20/50 System. In some embodiments, the cultured cells are formulated in suspension growth media, optionally with DMSO or similar solvent (e.g., 5 weight percent, 10 weight percent, or more). In some embodiments, formulations include cultured suspension HEK-293 cells of the invention at a concentration of approximately $1 \times 10^7$ cells/ml or more. Such cultured cells may further be stored under sterile conditions in cold storage. In some embodiments, the cultured cells undergo controlled-rate freezing by first freezing with dry ice and then freezing at liquid nitrogen temperatures.

Adherent HEK-293 Cell Line

Also provided according to embodiments of the invention is an isolated adherent HEK-293 cell deposited under the Budapest Treaty on Nov. 5, 2021 (ATCC Deposit No. PTA-127161). Further provided in embodiments of the invention are cell cultures that include adherent HEK-293 cells deposited under ATCC Deposit No. PTA-127161. As used herein, HEK-293 cells deposited under ATCC Deposit No. PTA-127161 may also be referred to as the "adherent HEK-293 cells of the invention." Also provided is a master cell bank including cells deposited as ATCC No. PTA-127161. In some embodiments of the invention, the HEK-293 master cell bank may be GMP-compliant (See, 21 CFR 210/211, 2003/94/EC).

In some embodiments, a cell line including the adherent HEK-293 cells of the invention may be cultured by any method now known or later discovered for growing adherent cells. Examples of adherent growth media include, without limitation, Dulbecco's Modified Eagle Medium (DMEM), Minimal Essential Medium, Modified Eagle's Medium, McCoy's 5a Medium, Leibovitz Medium, Nutrient medium F-10 and F-11 (RG Ham), Weymouth's Medium, and Grace's Medium. In some embodiments, the growth media is supplemented with fetal bovine and/or calf serum, for example, at a concentration of 5 weight percent, 10 weight percent, or more.

Any suitable adherent culturing method now known or later discovered may be used to culture the adherent HEK-293 cells of the invention. However, in some embodiments of the invention, adherent cells are cultured in static cell culture systems including Petri dishes and T-flasks. In some embodiments, T-flasks provide culture surface ranging from 25 to 225 cm². In some embodiments, adherent cells may be cultured in roller bottles or multilayer tissue culture flasks. Typically, the volume of the culture can be varied between 25 and 100%, which is equivalent to 125 and 500 ml for a roller bottle with a surface area of 850 cm², thus allowing higher product concentrations at lower culture volumes.

In some embodiments, the adherent cells of the invention are cells are incubated at a temperature in a range of about 35 to about 40° C. (e.g., 37° C.) for any suitable time (e.g., 24, 32, 40, 48 hours or more) and optionally under an atmosphere supplemented with carbon dioxide (e.g., at 5% or more $CO_2$ flow).

Methods of Producing Virus Vectors

The present invention further provides methods of producing virus vectors using the suspension or adherent HEK-293 cells of the invention. In some embodiments, provided are methods of producing AAV particles that include (a) providing to at least one suspension or adherent HEK-293 cell of the invention an AAV expression system; (b) culturing the at least one suspension or adherent HEK-293 cell under conditions in which AAV particles are produced; and, optionally, (c) isolating the AAV particles.

Any suitable AAV expression system may be used. As described above, an AAV expression system is a system of one or more polynucleotides that are sufficient, when introduced into a suitable host cell, to support the production of AAV. Conditions sufficient for the replication and packaging of the AAV particles can be, e.g., the presence of AAV sequences sufficient for replication of an AAV template and encapsidation into AAV capsids (e.g., AAV rep sequences and AAV cap sequences) and helper sequences from adenovirus and/or herpesvirus. The AAV template and AAV rep and cap sequences are provided under conditions such that virus vector comprising the AAV template packaged within the AAV capsid is produced in the cell. In some embodiments, a triple plasmid transfection system may be used.

The AAV replication and capsid sequences may be provided by any method known in the art. In some embodiments, the AAV rep/cap genes are expressed on a single plasmid. The AAV replication and packaging sequences need not be provided together, although it may be convenient to do so. Further, in some embodiments, the AAV rep/cap sequences will not be flanked by the TRs, to prevent rescue and/or packaging of these sequences. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal yet will maintain a high copy number throughout successive cell divisions (i.e., are stably integrated into the cell as extra-chromosomal elements, designated as an "EBV based nuclear episome," See, Margolski, *Curr. Top. Microbiol. Immun.* 158:67 (1992). As a further alternative, the rep/cap sequences may be stably incorporated into a cell.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the Ela or E3 regions of a deleted adenovirus). As another illustration, Palombo et al., *J Virol.* 72:5025 (1998), describes a baculovirus vector carrying a reporter gene flanked by the AAV TRs. EBV vectors may also be employed to deliver the template, as described above with respect to the rep/cap genes. In another representative embodiment, the AAV template is provided by a replicating rAAV virus. In still other embodiments, an AAV provirus comprising the AAV template is stably integrated into the chromosome of the cell. In particular embodiments, the AAV template comprises two AAV ITR sequences, which are located 5' and 3' to the heterologous nucleic acid sequence, although they need not be directly contiguous thereto. In some embodiments, the AAV template comprises an ITR that is not resolved by Rep to make duplexed AAV vectors as described in international patent publication WO 01/92551.

In some embodiments, to enhance virus titers, helper virus functions (e.g., adenovirus or herpesvirus) that promote a productive AAV infection can be provided to the cell. Helper virus sequences necessary for AAV replication are known in the art. In some embodiments, these sequences will be provided by a helper adenovirus or herpesvirus vector. Alternatively, the adenovirus or herpesvirus sequences can be provided by another non-viral or viral vector, e.g., as anon-infectious adenovirus miniplasmid that carries all of the helper genes that promote efficient AAV production as described by Ferrari et al., *Nature Med.* 3:1295 (1997), and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs. Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV template can also be provided as a separate replicating viral vector. For example, the AAV template can be provided by an AAV particle or a second recombinant adenovirus particle. In some embodiments, the AAV template is integrated into the cell as a provirus. Alternatively, the AAV template is provided by an EBV vector that is maintained within the cell as an extrachromosomal element (e.g., as an EBV based nuclear episome). The AAV rep/cap sequences and/or the AAV template can also be inserted into a deleted region (e.g., the Ela or E3 regions) of the adenovirus.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions. One other illustrative embodiment is described in Zhang et al., *Gene Ther.* 18:704 ((2001)), which describes a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (See, Conway et al., *Gene Ther.* 6:986 (1999) and WO 00/17377).

According to the methods of the invention, any culture conditions of the suspension or adherent HEK-293 cells of the invention in which AAV particles are produced may be used.

In some embodiments, culturing the cells under conditions in which AAV particles are produced includes culturing the suspension HEK-293 cells of the invention in suspension. In some embodiments, the suspension HEK-293 cells are cultured in animal component-free conditions. The animal component-free medium can be any animal component-free medium (e.g., serum-free medium) compatible with HEK-293 cells. Examples include, without limitation, SFM4Transfx-293 (Hyclone), Ex-Cell 293 (JRH Biosciences), LC-SFM (Invitrogen), and Pro293-S (Lonza), and Freestyle™ F-17 (Gibco). In representative embodiments, the method of the invention is completely scalable, so it can be carried out in any desired volume of culture medium, e.g., from 10 ml (e.g., in shaker flasks) to 10 L, 50 L, 100 L, or more (e.g., in bioreactors such as wave bioreactor systems and stirred tanks). In some embodiments, cells are incubated at a temperature in a range of about 35 to about 40° C. (e.g., 37° C.) in a shaker for 24, 32, 40, 48 hours or more and/or incubated in suspension growth media in a bioreactor for 24, 32, 40, 48 hours or more.

In some embodiments, adherent HEK-293 cells of the invention are cultured in an adherent culturing method known in the art. In some embodiments, a cell line including the adherent HEK-293 cells of the invention may be cultured by any method using adherent growth media include, without limitation, Dulbecco's Modified Eagle Medium (DMEM), Minimal Essential Medium, Modified Eagle's Medium, McCoy's 5a Medium, Leibovitz Medium, Nutrient medium F-10 and F-11 (RG Ham), Weymouth's Medium, and Grace's Medium. In some embodiments, the growth media is supplemented with fetal bovine and/or calf serum, for example, at a concentration of 5 weight percent, 10 weight percent, or more.

In some embodiments of the invention, adherent cells are cultured in static cell culture systems including Petri dishes and T-flasks. In some embodiments, T-flasks provide culture surface ranging from 25 to 225 cm$^2$. In some embodiments, adherent cells may be cultured in roller bottles or multilayer tissue culture flasks. Typically, the volume of the culture can be varied between 25 and 100%, which is equivalent to 125 and 500 ml for a roller bottle with a surface area of 850 cm$^2$, thus allowing higher product concentrations at lower culture volumes. In some embodiments, the adherent cells of the invention are cells are incubated at a temperature in a range of about 35 to about 40° C. (e.g., 37° C.) for any suitable time (e.g., 24, 32, 40, 48 hours or more) and optionally under an atmosphere supplemented with carbon dioxide (e.g., at 5% or more CO$_2$ flow).

In some embodiments, methods further include the step of collecting the virus vector from the culture. In one embodiment, the virus vector can be collected by lysing the cells, e.g., after removing the cells from the culture medium, e.g., by pelleting the cells. In another embodiment, the virus vector can be collected from the medium in which the cells are cultured, e.g., to isolate vectors that are secreted from the cells. Some or all of the medium can be removed from the culture one time or more than one time, e.g., at regular intervals during the culturing step for collection of rAAV (such as every 12, 18, 24, or 36 hours, or longer extended time that is compatible with cell viability and vector production), e.g., beginning about 48 hours post-transfection. After removal of the medium, fresh medium, with or without additional nutrient supplements, can be added to the culture. In one embodiment, the cells can be cultured in a perfusion system such that medium constantly flows over the cells and is collected for isolation of secreted rAAV. Collection of rAAV from the medium can continue for as long as the transfected cells remain viable, e.g., 48, 72, 96, or 120 hours or longer post-transfection. In certain embodiments, the collection of secreted rAAV is carried out with serotypes of AAV (such as AAV8 and AAV9), which do not bind or only loosely bind to the producer cells. In other embodiments, the collection of secreted rAAV is carried out with heparin binding serotypes of AAV (e.g., AAV2) that have been modified so as to not bind to the cells in which they are produced. Examples of suitable modifications, as well as rAAV collection techniques, are disclosed in U.S. Publication No. 2009/0275107, which is incorporated by reference herein in its entirety.

Clarified AAV lysate may be purified by any suitable known column chromatography method. The use of ion exchange chromatography has been shown to successfully purify several AAV serotypes. Brument et al. and Davidoff et al. used a two-column system to purify AAV serotypes 2, 5 and 8 (Brument et al., *Mol. Ther.* 6:678 (2002); Davidoff et al., *J. Virol. Meth.* 121:209 (2004)). Zolotukhin et al. showed that use of iodixanol in addition to ion exchange utilizing a Q-Sepharose column was able to purify serotypes 1, 2, and 5 (Zolotukhin et al., *Methods* 28:158 (2002)). Other various forms of chromatography may be used including methods described in the following references; Chahal et al., *J. Virol. Meth.* 139:61 (2007); Gao et al., *Hum. Gene Ther.* 11:2079 (2000); Hermens et al., *Hum. Gene Ther.* 10:1885 (1999); Kaludov et al., *Hum. Gene Ther.* 13:1235 (2002); Smith et al., *J. Virol. Meth.* 114:115 (2003); Zolotukhin et al., and *Gene Ther.* 6:973 (1999).

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. *Gene Ther.* 6:973 (1999)). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Methods of the invention are suitable for the production of all serotypes and chimeras of AAV now known or later discovered, e.g., AAV1, AAV2, AAV3, AAV4, AAV5, AAV6, AAV7, AAV8, AAV9, AAV10, AAV11, AAV12, AAV13, and any chimeras thereof. In certain embodiments, methods provide at least about $1.0 \times 10^3$ vector genome-containing particles per cell; in some embodiments, at least about $1.0 \times 10^4$ vector genome-containing particles per cell; in some embodiments, at least about $1.0 \times 10^5$ vector genome-containing particles per cell; in some embodiments, at least about $4 \times 10^5$ vector genome-containing particles per cell; and in some embodiments, at least about $8 \times 10^5$ vector genome-containing particles per cell, e.g., at least about $1 \times 10^5$, $1.5 \times 10^5$, $2 \times 10^5$, $3 \times 10^5$, $4 \times 10^5$, $5 \times 10^5$, $6 \times 10^5$, $7 \times 10^5$, $8 \times 10^5$ or $9 \times 10^5$ or more vector genome-containing particles per cell. In other embodiments, the method provides at least about $5 \times 10^{12}$ purified vector genome-containing particles per liter of cell culture, e.g., at least about $9 \times 10^{12}$, $1 \times 10^{13}$, $2 \times 10^{13}$, $3 \times 10^{13}$, or $4 \times 10^{13}$ or more purified vector genome-containing particles per liter of cell culture. In certain embodiments, the suspension HEK-293 cells of the invention can be used in an AAV production method that provides at least about $4 \times 10^5$ vector genome-containing particles per cell, e.g., at least about $8 \times 10^5$ vector genome-containing particles per cell. In certain embodiments, the adherent HEK-293 cells of the invention can be used in an AAV production method that provides at least about $1 \times 10^3$ vector genome-containing particles per cell, e.g., at least about $1 \times 10^4$ vector genome-containing particles per cell.

In some embodiments, quantitative polymerase chain reaction or qPCR may be used determine vector yields. Any suitable technique, including any suitable qPCR technique, may be used to determine the vector yield or vector genome.

Recombinant Virus Vectors

The virus vectors produced by the adherent or suspension HEK-293 cells of the invention may be useful for the delivery of nucleic acids to cells in vitro, ex vivo, and in vivo. In particular, the virus vectors can be advantageously employed to deliver or transfer nucleic acids to animal, including mammalian, cells. Any heterologous nucleic acid sequence(s) of interest may be delivered in the virus vectors produced by the present invention. Nucleic acids of interest include nucleic acids encoding polypeptides or RNAs, including reporter, therapeutic (e.g., for medical or veterinary uses), immunogenic (e.g., for vaccines), or diagnostic polypeptides or RNAs. As a further alternative, the heterologous nucleic acid can encode any polypeptide or RNA that is desirably produced in a cell in vitro, ex vivo, or in vivo. For example, the virus vectors may be introduced into cultured cells and the expressed gene product isolated therefrom.

The virus vectors produced according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

Having described the present invention, the same will be explained in greater detail in the following examples, which are included herein for illustration purposes only, and which are not intended to be limiting to the invention.

Example 1

Derivation of Suspension HEK-293 Cells from an Adherent HEK-293 Cell Line

A master cell bank (also referred to as PCB-293F-01) includes suspension HEK-293 cells of the invention. The suspension HEK-293 cells of the invention (ATCC No. PTA-127160 deposited Nov. 5, 2021) were derived from an adherent HEK-293 cell line from ATCC. To optimize AAV vector production yield, the original adherent HEK-293 cells were diluted to obtain single cells. Each cell was then expanded to generate a colonized cell line.

To generate the suspension HEK-293 cells, 4-passage sequential adaption assays were performed to wean a colonized adherent HEK-293 cell line from serum-containing DMEM media to an animal component-free expression medium (Serum-free FreeStyle™ F17 Expression Medium). The growth media for adaptation are as follows:

Passage 1: 75% serum-containing DMEM growth media/ 25% serum-free F17 expression media.
Passage 2: 50% serum-containing DMEM growth media/ 50% serum-free F17 expression media.
Passage 3: 25% serum-containing DMEM growth media/ 75% serum-free F17 expression media.
Passage 4: 100% serum-free F17 expression media.

For each passage, $2-3\times10^5$ cells/ml were inoculated in 10 cm tissue culture dishes and incubated at 37° C. for 3-4 days when the cell density reached $1-3\times10^6$ cells/ml. The adapted cells were then further cultured in serum-free F17 expression media for 3-4 days to obtain cells with a density of $1-3\times10^6$ cells/ml with a viability ≥95%. The cultures cells were then supplemented with 10% DMSO, aliquoted into sterile cryovials (1 ml/vial) and stored in a liquid nitrogen freezer.

To generate the PCB-293F-01 master cell bank (MCB), a stock cryovial suspension of the HEK-293 cells (ATTC No. PTA-127160) were thawed and then transferred to a 15 ml Comical centrifuge tube containing 5 ml of F17 growth media. The tube was centrifuged at 1,000 rpm for 5 minutes. The cell pellet was re-suspended in 10 ml F17 growth media, transferred to a 500 ml Corning® Erlenmeyer cell culture flask containing 100 ml of F17 growth media, and then incubated at 37° C. in a Multitron Incubator Shaker for 48 hours. The cultures were then transferred to a 5 L Labtainer™ BioProcess Container on Wave Bioreactor™ 20/50 System for 48 hours. The cell cultures were transferred into 500 ml sterile centrifuge bottles, and then centrifuged at 1,000 rpm for 10 minutes. The media was discarded by sterile vacuum aspiration and the cell pellets were re-suspended with F17 growth media. The viability of the cells was 98%. The cell suspension was formulated with F17 growth media and DMSO (10%) to $1\times10^7$ cells/ml. The formulated cell suspension was aliquoted by aseptic final fill into 2 ml sterile cryovials (1 ml/vial) with controlled rate freezing on dry ice, and then transferred to a liquid nitrogen freezer for final storage of the PCB-293F-01 MCB.

GMP-Compliant Release Tests of PCB-293F-01 MCB

The PCB-293F-01 MCB was tested for release by the BioReliance Corporation (Rockville, MD) in accordance with US FDA/EC Current Good Manufacturing Practice regulations (21 CFR 210/211, 2003/94/EC). The MCB passed all required release tests and is sterile and free of microbial, mycoplasma, endotoxin, and viral contaminants. The release test results qualify the PCB-293F-01 MCB to be used in cGMP rAAV vector manufacturing for clinical applications. A summary of tests is listed below:

DNA Fingerprinting of the PCB-293F-01 Cell lines with Multi Locus Probe 33.15: Under the hybridization conditions used, the MLP 33.15 generated a DNA profile of approximately 17 bands/loci greater than 3 kbp on digestion with Hae III. The profile for the test article was identical to the HEK-293 standard profile with the exception of an absent band at approximately 4 kb in the test article. Digestion with Hinf I and hybridization with the MLP 33.15 generated a DNA fingerprint profile of approximately 20 bands/loci greater than 3 kbp. The profile obtained for the test article was identical to the HEK-293 standard profile. Due to the minor differences observed, the band sharing frequency between the test article and the standard DNA fingerprint profiles was 94.4% for Hae III digested DNA and 100% for Hinf I digested DNA. The results obtained are consistent with the test article cell line being of HEK-293 (or closely related) origin with the minor differences observed arising as a result of genetic drift and/or the introduction of recombinant DNA sequences into the test article genome.

Test for the Presence of Agar-Cultivable and Non-Agar-Cultivable Mycoplasma: No mycoplasma was detected.

Evaluation of Reverse Transcriptase Activity by Ultra-centrifugation and Quantitative Fluorescent Product Enhanced Reverse Transcriptase (QFPERT) Assay: Negative.

Test for the Presence of Inapparent Viruses in Suckling Mice, Adult Mice, and Embryonated Hens' Eggs: Negative for the presence of adventitious viral contaminants.

28-Day In Vitro Assay for the Presence of Viral Contaminants: Negative for the presence of viral contaminants.

Real time Polymerase Chain Reaction Assay for the Detection of Human Metapneumonovirus (hMPV) Lineage A and Lineage B in Biological Samples: Negative for Human Metapneumonovirus (hMPV) lineage A and negative for Human Metapneumonovirus (hMPV) lineage B.

Detection of 14 Viruses by Real-Time Polymerase Chain Reaction Assays: Negative for the presence of HSV-1/ 2, B19, EBV, SV40, HHV5 (hCMV), HHV6, HHV7, HHV8, HBV, HIV-1, HIV-II, HTLV I/II, HCV, and HAV.

Microbial Examination of Non-Sterile Products: Qualification of Microbial Enumeration Tests Using a Spread Plate Method: Pass Qualification of the Test Article for the Detection of Agar-Cultivable Mycoplasma in Accordance with USP EP PCT/JP Requirements: No Mycoplasmastasis observed.

Assessing the Yields of rAAV Vector Production Using PCB-293F-01 MCB

The suspension HEK-293 cells of the invention (ATTC No. PTA-127160) were tested for the production of serotype 1-10 rAAV vectors by use of a triple plasmid transfection method. The cells were grown in 50 ml of Freestyle™ F17 growth media and transfected with ptr-CMV-GFP, pHELP, and AAV helper plasmids for AAV serotype 1-10 capsids, respectively. The rAAV-CMV-GFP vectors were then purified from the media and cell pellets using ion exchange chromatography and titrated by qPCR. The vector yield/ vector genome (vg) is shown in Table 2. The vector yields are obtained from the crude media and cell pellet, without purification. The results show differential vector yields among different serotypes in a range of $1.97 \times 10^5$ to $8.97 \times 10^5$ vg/cell. These results evidence that the PCB-293F-01 MCB is a relatively large producer for the majority of tested AAV serotypes ($3.71$-$8.97 \times 10^5$ vg/cell), with the exception of a moderate producer for AAV2 at $1.97 \times 10^5$ vg/cell.

TABLE 2

| Yield of rAAV vector production in PCB-293F-01 MCB | | | | | |
|---|---|---|---|---|---|
| AAV Serotypes | Number of cells | Vector yield* | | | |
| | | Media (vg) | Cell pellet (vg) | Total (vg) | vg/cell |
| 1 | $5 \times 10^7$ | $2.45 \times 10^{10}$ | $2.03 \times 10^{13}$ | $2.15 \times 10^{13}$ | $4.31 \times 10^5$ |
| 2 | $5 \times 10^7$ | $5.29 \times 10^9$ | $9.58 \times 10^{12}$ | $9.84 \times 10^{12}$ | $1.97 \times 10^5$ |
| 3 | $5 \times 10^7$ | $9.27 \times 10^9$ | $1.87 \times 10^{13}$ | $1.92 \times 10^{13}$ | $3.83 \times 10^5$ |
| 4 | $5 \times 10^7$ | $1.07 \times 10^{10}$ | $1.84 \times 10^{13}$ | $1.89 \times 10^{13}$ | $3.79 \times 10^5$ |
| 5 | $5 \times 10^7$ | $1.63 \times 10^{10}$ | $1.47 \times 10^{13}$ | $1.55 \times 10^{13}$ | $3.10 \times 10^5$ |
| 6 | $5 \times 10^7$ | $1.48 \times 10^{10}$ | $4.41 \times 10^{13}$ | $4.48 \times 10^{13}$ | $8.97 \times 10^5$ |
| 7 | $5 \times 10^7$ | $4.57 \times 10^{10}$ | $1.84 \times 10^{13}$ | $2.07 \times 10^{13}$ | $4.14 \times 10^5$ |
| 8 | $5 \times 10^7$ | $3.06 \times 10^{10}$ | $1.70 \times 10^{13}$ | $1.85 \times 10^{13}$ | $3.71 \times 10^5$ |
| 9 | $5 \times 10^7$ | $1.71 \times 10^{10}$ | $2.44 \times 10^{13}$ | $2.53 \times 10^{13}$ | $5.05 \times 10^5$ |
| 10 | $5 \times 10^7$ | $2.27 \times 10^{10}$ | $2.07 \times 10^{13}$ | $2.18 \times 10^{13}$ | $4.37 \times 10^5$ |

*Vector yield in 50 ml cultures

Example 2

Adherent HEK-293 Cell Line

A master cell bank (also referred to as HF1293) includes adherent HEK-293 cells of the invention. The adherent HEK-293 cells of the invention (ATTC No. PTA-127161 deposited Nov. 5, 2021) were tested for the production of certain rAAV vectors (serotypes AAV1, AAV2, AAV3, AAV5, AAV6, AAV8, and AVV9) by use of a triple plasmid transfection method. In doing so, the adherent HEK-293 cells of the invention were cultured in DMEM media supplemented with 10% fetal bovine serum or calf serum and incubated at 37° C. in an incubator with 5% $CO_2$ flow. The vector yield (vg/cell) for these certain AAV serotypes is shown in Table 3.

TABLE 3

| Yields of rAAV vector production in adherent HEK 293 cell line 293HF1 | | | |
|---|---|---|---|
| AAV Serotypes | Number of Preps* | Vector Yield (vg/cell)** | |
| | | Range | Means ± SD |
| AAV1 | 24 | $1.2 \times 10^3$-$3.3 \times 10^4$ | $1.5 \times 10^4 \pm 8.3 \times 10^3$ |
| AAV2 | 16 | $1.3 \times 10^3$-$7.2 \times 10^4$ | $2.7 \times 10^4 \pm 2.4 \times 10^4$ |
| AAV3 | 3 | $5.3 \times 10^3$-$5.9 \times 10^4$ | $2.6 \times 10^4 \pm 2.9 \times 10^4$ |
| AAV5 | 27 | $3.4 \times 10^3$-$5.7 \times 10^4$ | $2.4 \times 10^4 \pm 1.3 \times 10^4$ |
| AAV6 | 11 | $3.0 \times 10^3$-$5.4 \times 10^4$ | $1.1 \times 10^4 \pm 7.9 \times 10^3$ |
| AAV8 | 30 | $2.8 \times 10^3$-$7.9 \times 10^4$ | $2.1 \times 10^4 \pm 1.6 \times 10^4$ |
| AAV9 | 51 | $1.2 \times 10^3$-$3.3 \times 10^4$ | $4.2 \times 10^4 \pm 3.9 \times 10^4$ |

Number of AAV vector production by UNC Vector Core
**Vector yield after purification.

The results show differential vector yields among different serotypes in a range of $1.2 \times 10^3$ to $7.9 \times 10^4$ vg/cell.

To further assess the potential of the HF1293 master cell bank, the cells were compared with an adhesive HEK 293 cell line from ATCC (ATCC-CRL-1573) for the production of serotype 2, 5, 6, 8 and 9, by 3-plasmids co-transfection. The cells were grown in duplicates in 25 ml DMEM growth media in 15 cm tissue culture plates, and transfected with ptr-CMV-GFP, pHELP, and AAV helper plasmids for AAV serotype 2, 5, 6, 8, and 9 capsids respectively. The cell lysates were analyzed by qPCR to quantify the rAAV-CMV-GFP vectors. The vector yield is expressed as vector genome (vg). The results (Table 4) showed differential vector yield among different serotypes, at $1.5$-$4.2 \times 10^5$ vg/cell using HF1293 and $6.7 \times 10^4$-$1.9 \times 10^5$ vg/cell using ATCC-CRL-1573 cells. These results support the notion that the HF1293 cells are a more effective producer for all 5 tested AAV serotypes, compared to ATCC-CRL-1573 cells.

TABLE 4

| Yield comparison of rAAV vector production in HF1293 MCB and ATCC-CRL-1573 cells | | | | | |
|---|---|---|---|---|---|
| AAV Serotypes | No. cells | Vector yield | | | |
| | | HF1-293 | | ATCC-CRL-1573 | |
| | | Total | vg/cell | Total | vg/cell |
| 2 | 2E+7 | 3.0E+12 | 1.5E+05 | 1.4E+12 | 6.7E+04 |
| 5 | 2E+7 | 5.1E+12 | 2.6E+05 | 1.6E+12 | 8.1E+04 |
| 6 | 2E+7 | 8.4E+12 | 4.2E+05 | 2.6E+12 | 1.4E+05 |

TABLE 4-continued

Yield comparison of rAAV vector production
in HF1293 MCB and ATCC-CRL-1573 cells

| AAV | | Vector yield | | | |
| | | HF1-293 | | ATCC-CRL-1573 | |
| Serotypes | No. cells | Total | vg/cell | Total | vg/cell |
| --- | --- | --- | --- | --- | --- |
| 8 | 2E+7 | 6.6E+12 | 3.1E+05 | 3.9E+12 | 1.9E+05 |
| 9 | 2E+7 | 5.3E+12 | 2.7E+05 | 2.7E+12 | 1.4E+05 |

The foregoing is illustrative of the present invention and is not to be construed as limiting thereof. The invention is defined by the following claims, with equivalents of the claims to be included therein.

That which is claimed is:

1. An isolated suspension HEK-293 cell deposited as ATCC No. PTA-127160.

2. A method of producing AAV particles, comprising:
(a) providing to at least one suspension HEK-293 cell of claim 1 an AAV expression system;
(b) culturing the at least one suspension HEK-293 cell under conditions in which AAV particles are produced; and
(c) optionally isolating the AAV particles.

3. The method of claim 2, wherein the at least one suspension HEK-293 cell is cultured in suspension.

4. The method claim 2, wherein the at least one suspension HEK-293 cell is cultured in animal component-free conditions.

5. The method of claim 2, wherein step (c) comprises isolating the AAV particles from the at least one suspension HEK-293 cell.

6. The method of claim 2, wherein step (c) comprises isolating the AAV particles from a medium in which the at least one suspension HEK-293 cell is cultured.

7. The method of claim 2, wherein said AAV is selected from the group consisting of AAV1, AAV2, AAV3, AAV4, AAV5, AAV6, AAV7, AAV8, AAV9, AAV10, AAV11, AAV12, AAV13, a chimeric AAV, and a hybrid AAV.

8. The method of claim 2, wherein said AAV expression system comprises a recombinant AAV plasmid comprising a transgene, a packaging rep-cap-containing plasmid, and an adenovirus helper plasmid.

9. The method of claim 2, wherein the method provides at least about $1.5 \times 10^5$ purified vector genome-containing particles per cell.

10. The method of claim 2, wherein the method provides at least about $4 \times 10^5$ purified vector genome-containing particles per cell.

11. The method of claim 2, wherein the method provides at least about $9 \times 10^{12}$ purified vector genome-containing particles per liter of cell culture.

12. The method of claim 2, wherein the method provides at least about $2 \times 10^{13}$ purified vector genome-containing particles per liter of cell culture.

13. The method of claim 2, wherein said AAV expression system comprises a recombinant AAV plasmid comprising a transgene, a packaging rep-cap-containing plasmid, and an adenovirus helper plasmid.

14. The method of claim 2, wherein the method provides at least about $1 \times 10^4$ purified vector genome-containing particles per cell.

15. The method of claim 2, wherein the method provides at least about $1 \times 10^5$ purified vector genome-containing particles per cell.

16. An isolated adherent HEK-293 cell deposited as ATCC No. PTA-127161.

17. A method of producing AAV particles, comprising:
(a) providing to at least one adherent HEK-293 cell of claim 16 an AAV expression system;
(b) culturing the at least one adherent HEK-293 cell under conditions in which AAV particles are produced; and
(c) optionally isolating the AAV particles.

18. The method of claim 17, wherein the at least one adherent HEK-293 cell is cultured on a growth medium.

19. The method of claim 17, wherein step (c) comprises isolating the AAV particles from the at least one adherent HEK-293 cell.

20. The method of claim 17, wherein step (c) comprises isolating the AAV particles from a growth medium on which the at least one adherent HEK-293 cell is cultured.

21. The method of claim 17, wherein said AAV is selected from the group consisting of AAV1, AAV2, AAV3, AAV4, AAV5, AAV6, AAV7, AAV8, AAV9, AAV10, AAV11, AAV12, AAV13, a chimeric AAV, and a hybrid AAV.

*     *     *     *     *